United States Patent [19]

Schmidt et al.

[11] 4,243,409
[45] Jan. 6, 1981

[54] 1,2,4-OXADIAZOLE DERIVATIVES AND HERBICIDE COMPOSITION CONTAINING SAME

[75] Inventors: Erich Schmidt; Friedrich Arndt, both of Berlin, Fed. Rep. of Germany

[73] Assignee: Schering Aktiengesellschaft, Berlin and Bergkamen, ; DEX

[21] Appl. No.: 1,157

[22] Filed: Jan. 4, 1979

[30] Foreign Application Priority Data

Jan. 12, 1978 [DE] Fed. Rep. of Germany ....... 2801509

[51] Int. Cl.³ .................... A01N 43/82; C07D 271/06
[52] U.S. Cl. ......................................... 71/92; 548/131
[58] Field of Search ...................... 260/307 G; 71/92; 548/131

[56] References Cited

U.S. PATENT DOCUMENTS

| | | | |
|---|---|---|---|
| 3,270,029 | 8/1966 | Palazzo | 260/307 G |
| 3,575,997 | 4/1971 | Breuer | 260/307 G |
| 3,632,599 | 1/1972 | Zschochke et al. | 71/92 |
| 3,741,977 | 6/1973 | Boesch | 71/92 |
| 4,003,909 | 1/1977 | Narayanan et al. | 260/307 G |

Primary Examiner—Anton H. Sutto
Attorney, Agent, or Firm—Michael J. Striker

[57] ABSTRACT

A 1,2,4-oxadiazole derivative of the formula

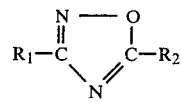

in which $R_1$ and $R_2$ are the same or different and are $C_1$–$C_8$-alkyl, $C_3$–$C_8$-cycloalkyl, halogeno-$C_1$–$C_3$-alkyl, phenyl, or phenyl substituted in one or several places by $C_1$–$C_4$ alkyl, and/or $C_1$–$C_4$-alkoxy and/or trihalogenomethyl and/or halogen and/or cyano or are phenyl-$C_1$–$C_3$-alkyl, provided that at least one of $R_1$ or $R_2$ is constituted by the group

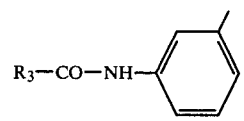

in which $R_3$ is $C_1$–$C_8$-alkyl, $C_3$–$C_8$-cycloalkyl, halogeno-$C_1$–$C_3$-alkyl, $C_1$–$C_6$-alkoxy, $C_1$–$C_4$-alkamino or di-$C_1$–$C_4$-alkamino. The compounds of the invention have a high activity against both mono- and di-cotyl weeds together with a high selectivity for agricultural plants such as rice, winter cereals, maize, cotton, sunflower, peanuts, soybeans, peas, alfalfa, clover and other leguminous plants. They may be applied in preemergence or postemergence application.

7 Claims, No Drawings

1,2,4-OXADIAZOLE DERIVATIVES AND HERBICIDE COMPOSITION CONTAINING SAME

BACKGROUND OF THE INVENTION

The invention relates to new 1,2,4-oxadiazole derivatives, a process for making the same and a herbicidal composition of selective activity in which these compounds form the active components.

Compositions with selective herbicidal activity are known. They have, however, frequently the shortcoming that their compatibility for agricultural plants is either limited to one, or at best, to a few types of such plants and that in addition they have an inadequate herbicidal activity against weeds.

It is therefore an object of the present invention to provide for a herbicidal compound and composition which in addition to a very strong activity against weeds, has also a broad spectrum of selectivity for agricultural plants.

SUMMARY OF THE INVENTION

This object is met by a herbicidal composition wherein at least one compound of the formula

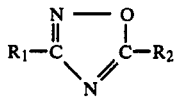

is present in which formula $R_1$ and $R_2$ are the same or different and are $C_1$-$C_8$-alkyl, $C_3$-$C_8$-cycloalkyl, halogeno-$C_1$-$C_3$-alkyl, phenyl, or are phenyl substituted in one or several places by $C_1$-$C_4$-alkyl and/or $C_1$-$C_4$-alkoxy and/or trihalogenomethyl and/or halogen and/or cyan or phenyl-$C_1$-$C_3$-alkyl, provided that at least one of $R_1$ or $R_2$ is constituted by the group

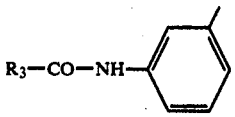

in which $R_3$ is $C_1$-$C_8$-alkyl, $C_3$-$C_8$-cycloalkyl, halogeno-$C_1$-$C_3$-alkyl, $C_1$-$C_6$-alkoxy, $C_1$-$C_4$-alkylamino or di-$C_1$-$C_4$-alkylamino.

The compounds are distinguished by a broad herbicidal activity both when applied to the soil and to the leaves. They can be used to control mono- and dicotyl weeds.

By using the compounds through preemergence and also in postemergence application, weeds present in agricultural fields of the types Sinapis, Stellaria, Senecio, Matricaria, Ipomoea, Chrysanthemum, Lamium, Centaurea, Amaranthus, Alopecurus, Lolium Lortulaca, Papaver, Kochia, Solanum, Escholzia, Datura, Bromus, Poa and other weeds can be kept under control.

To control seed-weeds the compounds are usually used in amounts of 1 kg of active agent per about 2.5 acres up to 5 g of active agent per 2.5 acres. The compounds are selective in cultures of agriculturally valuable plants such as rice, winter cereals, maize, cotton, sunflower, peanuts, soybeans, peas, alfalfa, clover and other leguminous plants.

The compounds of the invention can either be used individually or intermixed with each other or together with other active agents. If desired, other defoliants, plant protective agents or pesticides, may be added as desired.

If it is intended to further broaden the spectrum of activity, other herbicides may be added. For instance, such additional herbicides may be taken from the group of the triazines, aminotriazoles, anilides, diazines, uracils, aliphatic carboxylic acids and halo-carboxylic acids, substituted benzoic acids and aryloxycarboxylic acids, hydrazides, amides, nitriles, esters of such carboxylic acids, carbamic acid- and thiocarbamic acid esters, urea derivatives, 2,3,6-trichlorobenzyloxypropanol, rhodan containing agents and other additives. By other additives there may also be understood non-phytotoxic additives which result in a synergistic increase of the activity in herbicides such as wetting agents, emulsifiers, solvents and oily additives.

It is preferred to use the compounds or their mixtures in the form of compositions such as powders, spraying agents, granulates, solutions, emulsions or suspensions while adding liquid and/or solid carrier materials or diluents and, if desired, wetting agents, adhesion promoting agents, emulsifiers and/or dispersants.

Suitable liquid carrier materials are for instance water, aliphatic and aromatic hydrocarbons, such as, benzene, toluene, xylene, cyclohexanone, isophorone, dimethylsulfoxide, dimethylformamide, and furthermore mineral oil fractions.

As solid carrier materials there may be used mineral earths, for instance, tonsil, silicagel, talc, kaolin, attaclay, limestone, silicic acid and plant products, for instance flours.

There may also be added surface active agents, for instance, calciumlignosulfonate, polyoxyethylenealkylphenol ether, naphthalene sulfonic acids and their salts, phenolsulfonic acids and their salts, formaldehyde condensation products, fatty alcoholsulfates as well as substituted benz-sulfonic acids and their salts.

The proportion of the active agent or agents in the compositions can be varied over a broad range. The compositions may for instance contain about 5 to 95% by weight of active agent, about 95 to 5% by weight of liquid or solid carrier material, and if desired, and upon reduction of the other carrier materials, up to 20% by weight of surface active agents.

The application of the composition can be effected in conventional form, for instance with water as carrier material, in sprays of about 100 to 1000 liters per 2.5 acres. The compounds may be applied in the so-called "low-volume" and "ultra-low-volume" process and the application is also possible in the form of so-called microgranulates.

PREFERRED EMBODIMENTS

Among the compounds of the invention, those are distinguished by a particularly effective herbicidal action in which in the above-given formula, $R_1$ or $R_2$ are $C_1$-$C_6$-alkyl, preferably branched alkyl, particularly tertiary butyl, or are halogen-$C_1$-$C_6$-alkyl, preferably trifluoromethyl, provided that one or the other of $R_1$ or $R_2$ constitutes the group

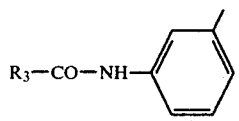

wherein $R_3$ is dimethylamino.

More particularly $R_1$ and $R_2$ may, for instance, be methyl, ethyl, n-propyl, isopropyl, n-butyl, sec.-butyl, isobutyl, tert.-butyl, n-pentyl, n-hexyl, n-heptyl, n-octyl, cyclopropyl, cyclopentyl, cyclohexyl, cyclooctyl, chloromethyl, dichloromethyl, trichloromethyl, 1-chloroethyl, 2-chloroethyl, phenyl, 3-methylphenyl, 4-methylphenyl, 3-ethylphenyl, 3-(n-propyl)-phenyl, 3-(n-butyl)-phenyl, 3-(tert.-butyl)-phenyl, 3-methoxyphenyl, 4-ethoxyphenyl, trifluoromethylphenyl, 3-chlorophenyl, 4-chlorophenyl, cyanophenyl, 3,5-dichlorophenyl, 2-methyl-4-chlorophenyl, benzyl and phenylethyl.

$R_3$ may for instance be methyl, ethyl, n-propyl, isopropyl, n-butyl, sec.-butyl, isobutyl, tert.-butyl, n-pentyl, n-hexyl, n-heptyl, n-octyl, cyclopropyl, cyclopentyl, cyclohexyl, cyclooctyl, chloromethyl, dichloromethyl, trichloromethyl, trifluoromethyl, 1-chloroethyl, 2-chloroethyl, methoxy, ethoxy, propoxy, isopropoxy, methylamino, ethylamino, n-propylamino, isopropylamino, dimethylamino and diethylamino.

An outstanding herbicidal activity have e.g. the following compounds:
3-[3-(3,3-dimethylureido)-phenyl]-5-trifluoromethyl-1,2,4-oxadiazole, and
3-[3-(3,3-dimethylureido)-phenyl]-5-tert.-butyl-1,2,4-oxadiazole.

PROCESS OF MAKING

The compounds of the invention can be made in various ways.

A. One way consists in reacting benzonitriles of the formula

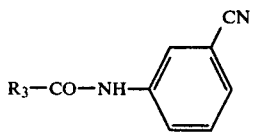

with hydroxylaminohydrochloride of the formula $$NH_2OH \cdot HCl$$

at a temperature of 25° to 100° C. in an organic solvent, preferably an alcohol such as ethanol or a mixture of alcohol and water and in the presence of an equimolar amount of a base, for instance, sodium- or potassium hydroxide or an alkali metal alcoholate, such as sodium ethylate. There are thus formed amidoximes of the formula

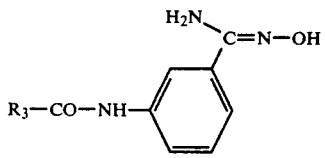

which latter are then reacted with a carboxylic acid halide or carboxylic acid anhydride of the formula $$R_2-CO-Cl$$

or $$R_2-CO-O-CO-R_2$$

at a temperature of 20° to 40° C. in an organic solvent such as diethylether, diisopropylether, dioxane, benzene or toluene, and, if desired, in the presence of an equimolar amount of an acid acceptor, e.g. triethylamine. Then, the reaction product is heated to temperatures up to 130° C., and the products of the invention are obtained by conventional isolation.

B. 3-benzamidoximes of the formula

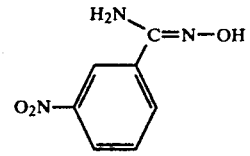

are reacted with a carboxylic acid halide or carboxylic acid anhydride of the formula $$R_2COCl$$

or $$R_2-CO-O-CO-R_2$$

at a temperature between 20° and 100° C. in an organic solvent, for instance an alcohol such as ethyl alcohol or a mixture of an alcohol with water and, if desired, in the presence of an equimolar amount of a base, for instance, sodium- or potassium hydroxide. There are thus formed 1,2,4-oxadiazole of the formula

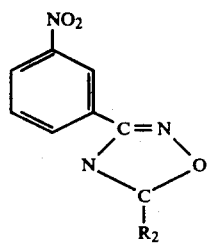

The latter are reduced by means of a reducing agent, for instance iron or zinc in an acid or neutral solution at temperatures of 20° to 40° C. to form the corresponding amino compound which then is reacted either with an acylating agent of the formula $$R_3-CO-Cl$$

or with an isocyanate of the formula $$R_3-N=C=O$$

at a temperature of 20° to 40° C. in an organic solvent, for instance diethylether, tetrahydrofuran, dioxane, acetone or acetonitrile, and if desired, in the presence of a base, for instance a tertiary base like pyridine or triethylamine. There is thus obtained the compound of the invention which is isolated in the conventional manner.

Alternatively, the hydrochloride of the amino compound may also be reacted with phosgene in an inert solvent like toluene or chlorobenzene at temperatures of 20° to 120° C. to form the corresponding isocyanate of the formula

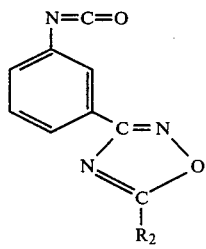

From the latter the compounds of the invention are then obtained with the corresponding $C_1$–$C_4$-alkylamines or di-$C_1$–$C_4$-alkylamines or $C_1$–$C_6$-alcohols and conventional isolation of the final end product.

C. Amidoximes of the formula

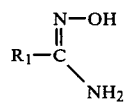

are reacted with equimolar amounts of 3-nitrobenzoylchloride of the formula

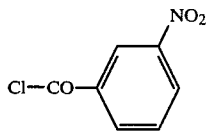

so as to form the corresponding 1,2,4-oxidazole of the formula

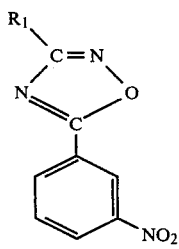

The reaction is carried out at a temperature of 20° to 40° C. in an organic solvent, for instance, diethylether, diisopropylether, dioxane, benzene, or toluene, and in the presence of a base, for instance, triethylamine or pyridine. Subsequently, the reaction product is reduced by means of a reducing agent, for instance iron or zinc in an acid or neutral solution at temperatures of 20° to 40° C. to obtain the corresponding amino compound which then is reacted either with an acylating agent of the formula $$R_3—CO—Cl$$

or with an isocyanate of the formula $$R_3—N=C=O$$

at a temperature of 20° to 40° C. in an organic solvent, for instance diethylether, tetrahydrofuran, dioxane, acetone or acetonitrile, and, if desired, in the presence of a base, for instance a tertiary base such as pyridine or triethylamine. There are then obtained the compounds of the invention by conventional isolation.

Alternatively, it is also possible to react the hydrochloride of the amino compound with phosgene in an inert solvent such as toluene or chlorobenzene at temperatures of 20° to 120° C. to form the corresponding isocyanate of the formula

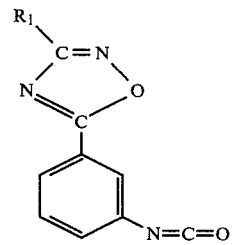

from which latter the compounds of the invention are then formed by reaction with the corresponding $C_1$–$C_4$-alkylamines or di-$C_1$–$C_4$-alkylamines or $C_1$–$C_6$-alcohols. The products of the invention are again isolated in conventional form.

In all of the above described processes $R_1$, $R_2$ and $R_3$ have the meaning as given above in the summary of the invention.

EXAMPLES

The invention will further be illustrated by the following examples.

EXAMPLE 1

3-[3-(3,3-dimethylureido)-phenyl]-5-trifluoromethyl-1,2,4-oxadiazole

Variant A 41.35 g (0.22 mol) of 3-(N,N-dimethylureido)-benzonitrile and 16.68 g (0.24 mol) of hydroxylammoniumchloride were suspended in 300 ml methanol. While stirring 9.60 g (0.24 mol) of sodium hydroxide were added and the mixture was subjected to boiling for 6 hours under reflux.

The reaction mixture was then filtered while hot and the filtrate was concentrated in a vacuum. The residue was subjected to repeated stirring with ether and was then dried at room temperature in a vacuum. The yield was 5-(N,N-dimethylureido)-benzamidoxime in an amount of 41.5 g=84.9% of the theoretical amount. The melting point of the compound was 186° C. (decomposition).

39.5 g (0.18 mol) of the last-obtained 3-(N,N-dimethylureido)-benzamidoxime were then suspended in 400 ml of tetrahydrofuran and were reacted during a period of 20 minutes while stirring with 25.2 ml (0.18 mol) of trifluoroacetanhydride. The reaction temperature during that step rose from 25° to about 38° C. Undissolved residue was filtered off, the filtrate was subjected to concentration by evaporation and the residue was recrystallized from acetic acid ester/hexane.

The yield was 3-[3-(3,3-dimethylureido)-phenyl]-5-trifluoromethyl-1,2,4-oxadiazole in an amount of 29.7 g=55% of the theoretical value. The melting point of the compound was 155° to 158° C.

Variant B 55.8 g (0.31 mol) of 3-nitrobenzamidoxime were dissolved in 900 ml of tetrahydrofuran and were reacted within a period of 1 hour by dropwise addition under stirring of 43.1 ml (0.31 mol) trifluoroacetic anhydride. During this operation the temperature rose by 10° C. After 3 hours the formation of the 1,2,4-oxadiazole was complete. The mass was then poured into 2 liter of ice water. The reaction product thereafter was extracted with acetic ester. The acetic ester phase was washed with water, dried on magnesium sulfate and stirred by revolving it. There were obtained 3-(3-nitrophenyl)-5-trifluoromethyl-1,2,4-oxadiazole in an amount of 52.8 g=65.7% of the theoretical value. The melting point of the compound was 77°–78° C.

49.6 g (0.19 mol) of the just-obtained 3-(3-nitrophenyl)-5-trifluoromethyl-1,2,4-oxadiazole were dissolved in 700 ml ethanol and were reacted with 80 ml $H_2O$ and 16.9 g (0.31 mol) of ammoniumchloride. 93.1 g (1.4 mol) of zinc powder were then added in batches while cooling by ice within a period of 30 minutes. The temperature during that operation should not exceed 30° C. After about 1 hour the reaction was complete.

The product was then filtered off the zinc and the alcohol was incorporated by revolving the mass. The residual oil was then taken up with acetic ester and the mass was washed twice with 300 ml water. The acetic ester phase was dried on magnesium sulfate, filtered and stirred by revolving it. The yield was 3-(3-aminophenyl)-5-trifluoromethyl-1,2,4-oxadiazole in an amount of 33 g=75.8 of the theoretical value. This compound was in the form of a yellow oil.

29.4 g (0.13 mol) of 3-(3-aminophenyl)-5-trifluoromethyl-1,2,4-oxadiazole were then dissolved in 75 ml pyridine and were reacted dropwise with 13.8 ml (0.15 mol) of dimethylcarbamoylchloride. The reaction temperature during this operation rose to a maximum of 40° C. At this temperature the mass was subjected to further stirring for 2 hours. Subsequently, the mass was poured onto 1 liter of water and the product was extracted with acetic ester. The organic phase was washed twice with 300 ml water, dried on magnesium sulfate and stirred with a rotating movement.

The crude product was recrystallized from acetic ester/hexane. The yield was 24.3 g=45% of the theoretical value of 3-[3-(3,3-dimethylureido)-phenyl]-5-trifluoromethyl-1,2,4-oxadiazole; melting point 155° to 158° C.

EXAMPLE 2

3-butyl-5-[3-(3,3-dimethylureido)-phenyl]-1,2,4-oxadiazole 11.6 g (0.1 mol) of valeric acid amidoxime were dissolved in 300 ml of tetrahydrofuran and reacted with 13.6 ml (0.1 mol) of triethylamine. 17.4 g (0.1 mol) of 3-nitrobenzoylchloride were then added dropwise while stirring. The reaction temperature during this step rose to a maximum of 35° C. Stirring was then continued for 3 hours. The mass was then separated from the triethylaminohydrochloride by suction and the filtrate was subjected to stirring by a rotating movement. The oily residue was taken up in 300 ml toluene, reacted with 300 mg p-toluenesulfonic acid and heated under reflux for 8 hours with a water separator. After cooling the reaction mixture was filtered and the filtrate was subjected to rotary stirring. The yield was 3-butyl-5-(3-nitrophenyl)-1,2,4-oxadiazole in an amount of 19.7 g=96% of the theoretical value; $n_D20=1.5520$.

12.3 g of (0.05 mol) of 3-butyl-5-(3-nitrophenyl)-1,2,4-oxadiazole were dissolved in a mixture of 250 ml ethanol and 25 ml water and were reacted with 4.5 g (0.085 mol) of ammonium chloride. 25.0 g (0.38 mol) of zinc powder were then added batchwise while stirring. The reaction temperature during that step rose to between 35° and 40° C. Stirring was continued for an hour. Subsequently, the mass was separated from the zinc by suction and the filtrate was subjected to rotary stirring. The residue was taken up with 200 ml of ether. The solution was washed twice with 50 ml of water, dried on magnesium sulfate, and filtered. The filtrate was then subjected to rotary stirring. The yield was 5-(3-aminophenyl)-3-butyl-1,2,4-oxadiazole in an amount of 8.2 g=75.9% of the theoretical value; $n_D20=1.5735$.

8.0 g (0.037 mol) of 5-(3-aminophenyl)-3-butyl-1,2,4-oxadiazole were dissolved in 15 ml pyridine and were reacted with 3.4 ml (0.037 mol) of dimethylcarbamoylchloride. The reaction was complete after stirring for 8 hours at room temperature. The mass was then reacted with about 100 ml ice water resulting in precipitation of the reaction product. The reaction produce was removed by suction, subjected to drying at 50° C. in a vacuum and recrystallized from diisopropylether. There were obtained 8.3 g=77.5% of the theoretical value of 3-butyl-5-[3-(3,3-dimethylureido)-phenyl]-1,2,4-oxadiazole; m.p. 108° to 110° C.

EXAMPLE 3

3-[3-(3-methylureido)-phenyl]-5-trifluoromethyl-1,2,4-oxadiazole 23 g (0.1 mol) of 3-(3-aminophenyl)-5-trifluoromethyl-1,2,4-oxadiazole as obtained as intermediate product in variant B of Example 1 were dissolved in 60 ml diethylether and were reacted after addition of a catalytic amount of triethylamine with 6.5 ml (0.1 mol) of methylisocyanate upon stirring and water cooling. The reaction temperature in this step rose to a maximum of 30° C. The reaction was complete after 1 hour. The solid reaction product was removed by suction, was recrystallized from acetonitrile and dried in a vacuum. There were obtained 19 g=66.5% of the theoretical value of 3-[3-(3-methylureido)-phenyl]-5-trifluoromethyl-1,2,4-oxadiazole; m.p. 141° to 143° C.

The following compounds were obtained in a manner analogous to the compounds described in the preceding examples.

| Compound | Physical Constants |
| --- | --- |
| 3-(3-n-propoxycarbonylamino)-phenyl-5-trifluoromethyl-1,2,4-oxadiazole | m.p.: 80°–82° C. |
| 3-[3-(3,3-dimethylureido)-phenyl]-5-trifluoromethyl-1,2,4-oxadiazole | m.p.: 163°–165° C. (decomposition) |
| 3-[3-(3-isopropylureido)-phenyl]-5-trifluoromethyl-1,2,4-oxadiazole | m.p.: 171°–173° C. |
| 3-[3-(3-ethylureido)-phenyl]-5-methyl-1,2,4-oxadiazole | m.p.: 141°–142° C. |
| 3-[3-(3-isopropylureido)-phenyl]-5-methyl-1,2,4-oxadiazole | m.p.: 183°–185° C. |
| 5-ethyl-3-[3-(3,3-dimethylureido)-phenyl]-1,2,4-oxadiazole | m.p.: 154°–156° C. |
| 5-cyclopropyl-3-[3-(3,3-dimethylureido)- | |

-continued

| Compound | Physical Constants |
|---|---|
| phenyl]-1,2,4-oxadiazole | m.p.: 148°–150° C. |
| 5-tert.-butyl-3-[3-(3,3-dimethyl-ureido)-phenyl]-1,2,4-oxadiazole | m.p.: 117°–120° C. |
| 3-[3-(3,3-dimethylureido)-phenyl]-5-isopropyl-1,2,4-oxadiazole | m.p.: 86°–90° C. |
| 3-[3-(3,3-dimethylureido)-phenyl]-5-propyl-1,2,4-oxadiazole | m.p.: 100°–104° C. |
| 3-[3-(3,3-dimethylureido)-phenyl]-5-(2-methylpropyl)-1,2,4-oxadiazole | m.p.: 65°–70° C. |
| 3-[3-(3,3-dimethylureido)-phenyl]-5-trichloromethyl-1,2,4-oxadiazole | m.p.: 130°–134° C. |
| 5-cyclohexyl-3-[3-(3,3-dimethyl-ureido)-phenyl]-1,2,4-oxadiazole | m.p.: 143°–146° C. |
| 5-benzyl-3-[3-(3,3-dimethylureido)-phenyl]-1,2,4-oxydiazole | m.p.: 153°–156° C. |
| 3-[3-(3,3-dimethylureido)-phenyl]-5-(3-methylphenyl)-1,2,4-oxadiazole | m.p.: 174°–177° C. |
| 3-[3-(3,3-dimethylureido)-phenyl]-5-(4-methylphenyl)-1,2,4-oxadiazole | m.p.: 203°–207° C. |
| 5-(dichloromethyl)-3-[3-(3,3-dimethyl-ureido)-phenyl]-1,2,4-oxadiazole | m.p.: 110°–114° C. |
| 5-(4-tert.-butylphenyl)-3-[3-(3,3-di-methylureido)-phenyl]-1,2,4-oxadiazole | m.p.: 156°–160° C. |
| 5-(4-chlorophenyl)-3-[3-(3,3-dimethyl-ureido)-phenyl]-1,2,4-oxadiazole | m.p.: 189°–190° C. |
| 5-tert.-butyl-3[(3-methoxycarbonyl-amino)-phenyl]-1,2,4-oxadiazole | m.p.: 86°–89° C. |
| 3-[3-(cyclopropylcarbonylamino)-phenyl]-5-tert.butyl-1,2,4-oxadiazole | m.p.: 75°–80° C. |
| 3-[3-(butyrylamino)-phenyl]-5-tert.-butyl-1,2,4-oxadiazole | m.p.: 85°–90° C. |
| 3-[3(3,3-diethylureido)-phenyl]-5-tert.-butyl-1,2,4-oxadiazole | m.p.: 132°–135° C. |
| 3-[3-(3,3-dimethylureido)-phenyl]-5-phenyl-1,2,4-oxadiazole | m.p.: 159°–163° C. |
| 3-tert.-butyl-5-[3-(3,3-dimethyl-ureido)-phenyl]-1,2,4-oxadiazole | m.p.: 121°–123° C. |
| 3-tert.butyl-5-[3-(3-methylureido)-phenyl]-1,2,4-oxadiazole | m.p.: 170°–174° C. |
| 5-chloromethyl-3-(3-cyclopropyl-car-bonylaminophenyl)-1,2,4-oxadiazole | m.p.: 134°–137° C. |
| 3-(3-cyclopropylcarbonylaminophenyl)-5-methyl-1,2,4-oxadiazole | m.p.: 171°–174° C. |
| 3-(3-cyclopropylcarbonylaminophenyl)-5-trifluoromethyl-1,2,4-oxadiazole | m.p.: 138°–142° C. |
| 3-[3-(3,3-dimethylureido)-phenyl]-5-phenyl-1,2,4-oxadiazole | m.p.: 159°–163° C. |

The compounds of the invention had a good solubility in acetic acid ethylester, acetone and alcohol. However, their solubility was only moderate in benzene and they were virtually insoluble in saturated hydrocarbons and water.

MANNER OF USE AND ACTIVITY TESTS

The following examples will further illustrate the uses and activity of the compounds of the invention.

EXAMPLE 4

The compounds listed in the Table 1 below were sprayed onto mustard and tomatoes as test plants in a preemergence and postemergence application in amounts of 5 kg of active agent per about 2.5 acres emulsified in 500 liters of water per 2.5 acres.

The results of the treatment were evaluated after 3 weeks on a scale from 0=no effect, to 4=total destruction of the plants. As appears from the table normally a total destruction of the test plants was accomplished.

This test is a laboratory experiment in which mustard and tomatoes as test plants represent or simulate an undesired growth. These tests therefore are made to permit an evaluation of suitable control activities.

TABLE I

| Compounds | Postemergence application | |
|---|---|---|
| | mustard | tomato |
| 3-[3-(3-methylureido)-phenyl]-5-trifluoromethyl-1,2,4-oxadiazole | 4 | 4 |
| 3-(3-n-propoxycarbonylamino)-phenyl-5-trifluoromethyl-1,2,4-oxadiazole | 4 | 4 |
| 3-[3-(3,3-dimethylureido)-phenyl]-5-trifluoromethyl-1,2,4-oxadiazole | 4 | 4 |
| 3-[3-(3,3-dimethylureidophenyl)]-5-methyl-1,2,4-oxadiazole | 4 | 4 |
| 5-ethyl-3-[3-(3,3-dimethylureido)-phenyl]-1,2,4-oxadiazole | 4 | 4 |
| 5-cyclopropyl-3-[3-(3,3-dimethylureido)-phenyl]-1,2,4-oxadiazole | 4 | 4 |
| 5-tert.-butyl-3-[3-(3,3-dimethylureido)-phenyl]1,2,4-oxadiazole | 4 | 4 |
| 3-[3-(3,3-dimethylureido)-phenyl]-5-isopropyl-1,2,4-oxadiazole | 4 | 4 |
| 3-[3-(3,3-dimethylureido)-phenyl]-5-propyl-1,2,4-oxadiazole | 4 | 4 |
| 3-[3-(3,3-dimethylureido)-phenyl]-5-(2-methylpropyl)-1,2,4-oxadiazole | 4 | 4 |
| 5-cyclohexyl-3-[3-(3,3-dimethylureido)-phenyl]-1,2,4-oxadiazole | 4 | 4 |
| 5-benzyl-3-[3-(3,3-dimethylureido)-phenyl]-1,2,4-oxadiazole | 4 | 4 |
| 3-[3-(3,3-dimethylureido)-phenyl]-5-(3-methylphenyl)-1,2,4-oxadiazole | 4 | 4 |
| 5-(dichloromethyl)-3-[3-(3,3-dimethylureido)-phenyl]-1,2,4-oxadiazole | 4 | 4 |
| 5-(tert.-butylphenyl)-3-[3-(3,3-dimethylureido)-phenyl]-1,2,4-oxadiazole | 4 | 4 |
| 5-(4-chlorophenyl)-3-[3-(3,3-dimethylureido)-phenyl]-1,2,4-oxadiazole | 4 | 4 |
| 5-tert.-butyl-3-[3-(methoxycarbonyl-amino)-phenyl]-1,2,4-oxadiazole | 4 | 4 |
| 3-[3-(cyclopropylcarbonylamino)-phenyl]-5-tert.-butyl-1,2,4-oxadiazole | 4 | 4 |
| 3-[3-(butyrylamino)-phenyl]-5-tert.-butyl-1,2,4-oxadiazole | 4 | 4 |
| 3-(n-butyl)-5-[3-(3,3-dimethylureido)-phenyl]-1,2,4-oxadiazole | 4 | 4 |
| 3-[3-(3,3-diethylureido)-phenyl]-5-tert.-butyl-1,2,4-oxadiazole | 4 | 4 |
| 3-[3-(3,3-dimethylureido)-phenyl]-5-phenyl-1,2,4-oxadiazole | 4 | 4 |
| 3-tert.-butyl-5-[3-(3,3-dimethylureido)-phenyl]-1,2,4-oxadiazole | 4 | 4 |
| 3-tert.-butyl-5-[3-(3-methylureido)-phenyl]-1,2,4-oxadiazole | 4 | 4 |
| 5-chloromethyl-3-(3-cyclopropyl-carbonylaminophenyl)-1,2,4-oxadiazole | 4 | — |
| 3-(3-cyclopropylcarbonylaminophenyl)-5-methyl-1,2,4-oxadiazole | 4 | 4 |
| 3-(3-cyclopropylcarbonylaminophenyl)-5-trifluoromethyl-1,2,4-oxadiazole | 4 | — |
| 3-[3-(3,3-dimethylureido)-phenyl]-5-phenyl-1,2,4-oxadiazole | 4 | 4 |

EXAMPLE 5

The plants listed in the Table 2 below were treated in a hothouse prior to emergence with the agents also listed in the table. The compounds were applied as aqueous solutions in amounts of 1 kg of active agent per about 2.5 acres in 500 liter water for the same area and were spread uniformly onto the soil.

The results appearing from the table show that the compounds of the invention as distinguished from the compound of the British Pat. No. 913,383 which is used as comparison compound, show a higher activity at the same selectivity. For the evaluation of the test results a scale was used in which 0 was equal to total destruction of the plant and 10 was equal to no damage to the plant.

TABLE II

| Compounds of the Invention | wheat | maize | rice | soy-beans | pota-toes | Lam-ium a. | Cent-aurea C. | Amar-anthus r. | Chry-San-the-mum s. | Ipo-moea p. | Poly-gonum l. | Alo-pecurus m. |
|---|---|---|---|---|---|---|---|---|---|---|---|---|
| 3-[3-(3,3-dimethylureido)-phenyl]-5-trifluoromethyl-1,2,4-oxadiazole | 10 | 10 | 10 | 10 | 10 | 0 | 0 | 0 | 0 | 0 | 0 | 0 |
| 3-[3-(3,3-dimethylureido-phenyl)]-5-tert.-butyl-1,2,4-oxadiazole | 10 | 10 | 10 | 10 | 10 | 0 | 0 | 0 | 0 | 0 | 0 | 0 |
| Comparison Compound (British Patent 913,383) N'-4-(4-chlorophenoxy)-phenyl-N,N-dimethyl urea | 10 | 10 | 10 | 10 | 10 | 1 | 3 | 3 | 4 | 6 | 3 | 8 |
| Untreated | 10 | 10 | 10 | 10 | 10 | 10 | 10 | 10 | 10 | 10 | 10 | 10 |

EXAMPLE 6

The plants listed below in Table 3 were treated in a hothouse after emergence with the compounds of the invention in amounts of 1 kg of active agent per 2.5 acres. The compounds for this purpose were sprayed onto the plants in a uniform manner.

The results of this test in the evaluation after 3 weeks likewise show a high selectivity to the tested agricultural plants together with a high activity against weeds. The evaluation of the treatment was effected on a scale in which 0 was equal to total destruction, and 10 was equal to no damage to the plant.

TABLE III

| Compounds of the Invention | pea-nuts | rice | Kochia sp. | Escholtzia sp. | Da-tura sp. | Ipo-moea sp. | Se-taria sp. | Digit-aria sp. | Euph-orbia sp. |
|---|---|---|---|---|---|---|---|---|---|
| 3-[3-(3,3-dimethylureido)-phenyl]-5-trifluoromethyl-1,2,4-oxadiazole | 10 | 10 | 0 | 0 | 0 | 0 | 0 | 0 | 0 |
| 3-[3-(3,3-dimethylureido-phenyl)]-5-tert.butyl-1,2,4-oxadiazole | 10 | 10 | 0 | 0 | 0 | 0 | 0 | 0 | 0 |
| Untreated | 10 | 10 | 10 | 10 | 10 | 10 | 10 | 10 | 10 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A selective herbicidal composition comprising about 5 to 95% by weight of at least one of compounds selected from the group consisting of 3-[3-(cyclopropylcarbonylamino)-phenyl]-5-tert.-butyl-1,2,4-oxadiazole, 3-[3-(butyrylamino)-phenyl]-5-tert.-butyl-1,2,4-oxadiazole, 5-chloromethyl-3-(3-cyclopropylcarbonylaminophenyl)-1,2,4-oxadiazole, 3-(3-cyclopropylcarbonylaminophenyl)-5-methyl-1,2,4-oxadiazole, and 3-(3-cyclopropylcarbonylaminophenyl)-5-trifluoromethyl-1,2,4-oxadiazole; and about 95 to 5% by weight of a liquid or solid carrier material.

2. The herbicidal composition of claim 1 which includes up to 20% by weight of a surface active agent upon a corresponding reduction of the liquid or solid carrier materials.

3. The compound which is 3-[3-(cyclopropylcarbonylamino)-phenyl]-5-tert.-butyl-1,2,4-oxadiazole.

4. The compound which is 3-[3-(butylrylamino)-phenyl]-5-tert.-butyl-1,2,4-oxadiazole.

5. The compound which is 5-chloromethyl-3-(3-cyclopropylcarbonylaminophenyl)-1,2,4-oxadiazole.

6. The compound which is 3-(3-cyclopropylcarbonylaminophenyl)-5-methyl-1,2,4-oxadiazole.

7. The compound which is 3-(3-cyclopropylcarbonylaminophenyl)-5-trifluoromethyl-1,2,4-oxadiazole.

* * * * *